(12) United States Patent
Robrish

(10) Patent No.: US 7,705,976 B2
(45) Date of Patent: Apr. 27, 2010

(54) METHOD FOR RECOGNIZING PATTERNS FROM ASSAY RESULTS

(75) Inventor: Peter R. Robrish, San Francisco, CA (US)

(73) Assignee: Alverix, Inc., San Jose, CA (US)

( * ) Notice: Subject to any disclaimer, the term of this patent is extended or adjusted under 35 U.S.C. 154(b) by 261 days.

(21) Appl. No.: 11/443,998

(22) Filed: May 31, 2006

(65) Prior Publication Data
US 2007/0279620 A1    Dec. 6, 2007

(51) Int. Cl.
*G01M 11/00* (2006.01)

(52) U.S. Cl. .................. 356/124.5; 356/124; 702/19; 702/22; 702/25

(58) Field of Classification Search .......... 356/124, 356/124.5; 702/19, 22, 25
See application file for complete search history.

(56) References Cited

U.S. PATENT DOCUMENTS

| | | | | |
|---|---|---|---|---|
| 4,139,303 A | * | 2/1979 | Carlson et al. ........... 356/71 |
| 4,395,312 A | * | 7/1983 | McCreery et al. ........ 205/701 |
| 5,506,676 A | * | 4/1996 | Hendler et al. .......... 356/237.1 |
| 5,629,766 A | * | 5/1997 | Kaplan .................... 356/124.5 |
| 6,766,817 B2 | | 7/2004 | da Silva | |
| 6,918,404 B2 | | 7/2005 | Dias da Silva | |
| 7,066,586 B2 | | 6/2006 | da Silva | |

OTHER PUBLICATIONS

U.S. Appl. No. 11/019,183 (Title: A Method and Apparatus for Reading an Assay Using Low Resolution Detection), filed Dec. 23, 2004, Robrish.

* cited by examiner

*Primary Examiner*—Gregory J Toatley, Jr.
*Assistant Examiner*—Iyabo S Alli
(74) *Attorney, Agent, or Firm*—K&L Gates, LLP

(57) ABSTRACT

A Fourier transform optical detection system for use with a test assay that has a sensitivity pattern, the detection system including a lens having a Fourier transform plane and detectors located in the Fourier transform plane positioned in an arrangement of a Fourier transform pattern of the sensitivity pattern.

18 Claims, 12 Drawing Sheets

METHOD FOR RECOGNIZING PATTERNS FROM ASSAY RESULTS

BACKGROUND

Currently, assays are read by human eye or a high cost imaging system. Assay readings done by eye are based on individual human judgment and therefore are subject to human error. Assays readings done by imaging systems require expensive detection systems. The purpose of reading these assays is to determine whether a test sample of biological or chemical material being assayed includes a particular analyte, or a derivative or constituent of the analyte. The particular analyte that is the subject of the assay is referred to as the analyte of interest. The test sample may include biological material such as urine, saliva, blood plasma, or the like. The test sample may include chemical material such as rainwater, sludge, or the like.

An assay is performed using a substrate having a sensitive region patterned on the surface of the substrate. Such substrates are known in the art, and the sensitive region is formed by a chemical treatment or a physical manipulation of the surface. The pattern of the sensitive region includes one or more shapes, for example, a circular shape with a diameter of approximately one centimeter (cm).

The substrate is typically made of silicon or glass and has a smooth surface. The surface of the substrate includes a sensitive region that reacts to exposure to an analyte of interest. The sensitive region is indistinguishable from the substrate outside the sensitive region until the sensitive region is exposed to the analyte of interest. The sensitive region will react to exposure of the sensitive region to an analyte of interest.

Detection of the reaction of the sensitive region upon exposure to the analyte of interest is performed by human eye or high-cost, high-resolution detection systems that determine the shape of the sensitive region upon exposure to the analyte of interest.

A human observes the sensitive region to determine if exposure to the sample resulted in a change in the appearance of the sensitive region relative to the rest of the substrate. If there was a sufficient change, the observer concludes that the sensitive region was exposed to the analyte of interest and thus, that the analyte of interest was included in the sample. When readings are made by the human eye to determine an exposure of the sensitive region to an analyte of interest, the readings may not be consistent and may be prone to error.

When assays are read by high-resolution systems, such as a charge-coupled device (CCD) systems and some CMOS-based system, the determination of an exposure of the sensitive region to of a analyte of interest is determined by a reading across the entire substrate to determine the shape and location of the sensitive region exposed to the analyte of interest. Such systems may be consistent and relatively error free. However, the equipment is expensive and such detailed determination is unnecessary.

Application Ser. No. 11/019,183 filed by the applicant on Dec. 23, 2004 (also referred to here as the "11/019,183 Application") describes a low resolution detection system that is strategically arranged in the image plane of a lens to detect illumination from reactive regions in a test assay in which the reactive regions for different analytes have different shapes, such as circular shapes, square shapes and/or rectangular shapes. The detection is done in the image plane of the lens using a priori knowledge of the shape for each reactive material in the test assay.

A market demand exists for a simple, consistent and inexpensive system to determine whether a test sample of biological or chemical material being assayed includes an analyte of interest.

SUMMARY

A first aspect of the present invention provides a Fourier transform optical detection system for use with a test assay that has a sensitivity pattern. The detection system includes a lens having a Fourier transform plane and detectors located in the Fourier transform plane positioned in an arrangement of a Fourier transform pattern of the sensitivity pattern.

A second aspect of the present invention provides a method of increasing a signal to noise ratio during a measurement of a test assay using a Fourier transform detection system. The method includes receiving light having a sensitivity pattern at a lens having a Fourier transform plane and detecting light at intensity peaks of a Fourier transform pattern of the sensitivity pattern in the Fourier transform plane.

A third aspect of the present invention provides a test assay for detecting an analyte. The assay includes a substrate and detection regions arranged in a Fourier transformable pattern on the substrate. The detection regions react with the analyte and emit light, transmit light or reflect light in the Fourier transformable pattern. The Fourier transformable pattern has at least one intensity peak with a contrast greater than 0.5 when Fourier transformed.

DRAWINGS

In accordance with common practice, the various described features are not drawn to scale but are drawn to emphasize features relevant to the present invention. Reference characters denote like elements throughout figures and text.

DETAILED DESCRIPTION

In the following detailed description, reference is made to the accompanying drawings that form a part hereof, and in which is shown by way of illustration specific illustrative embodiments in which the invention may be practiced. These embodiments are described in sufficient detail to enable those skilled in the art to practice the invention, and it is to be understood that other embodiments may be utilized and that logical changes may be made without departing from the scope of the present invention. The following detailed description is, therefore, not to be taken in a limiting sense.

Figure 1A:
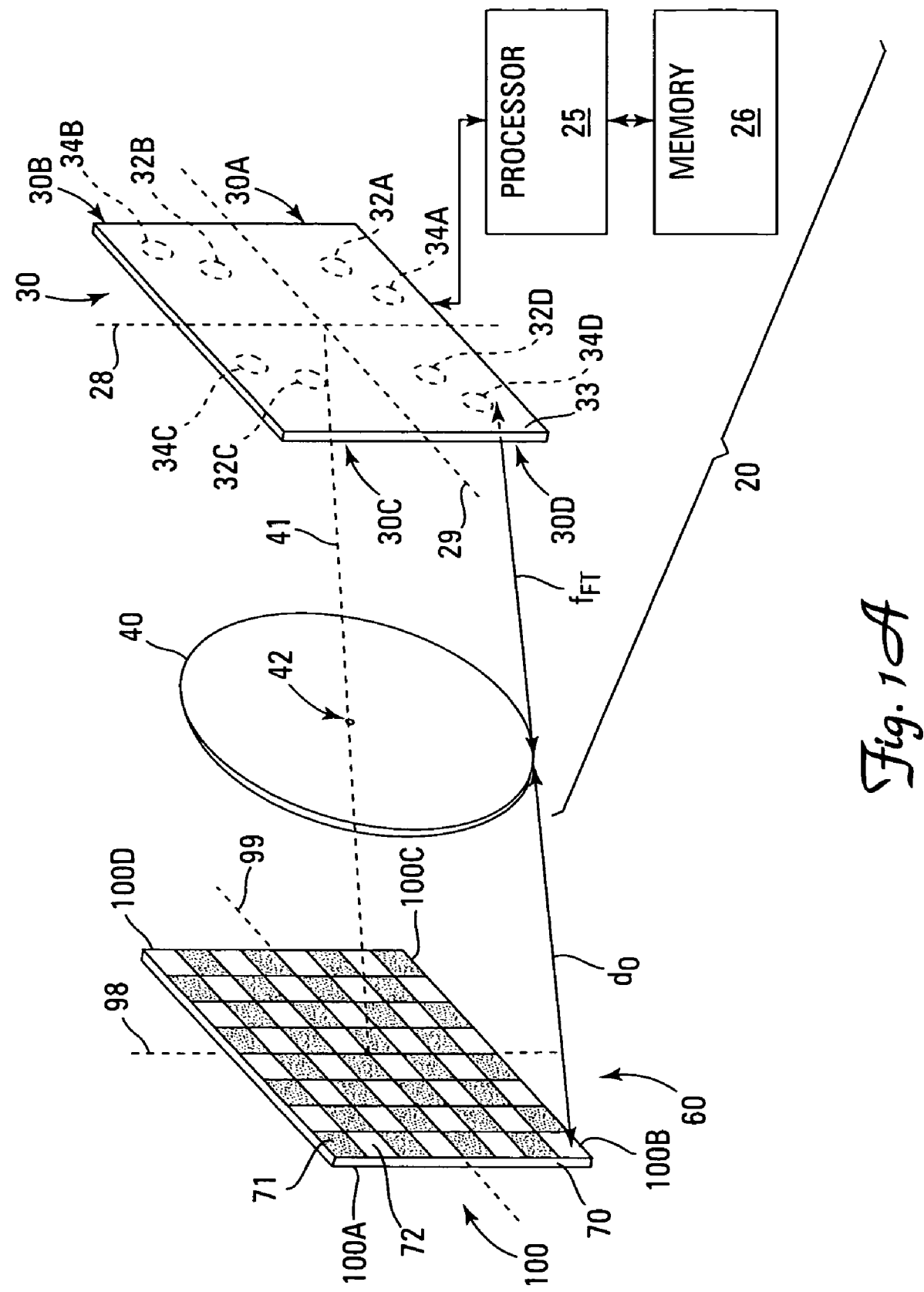
FIGS. 1A and 1B are views of one embodiment of a Fourier transform optical detection system for use with a test assay having a sensitivity pattern.
Figure 1B:
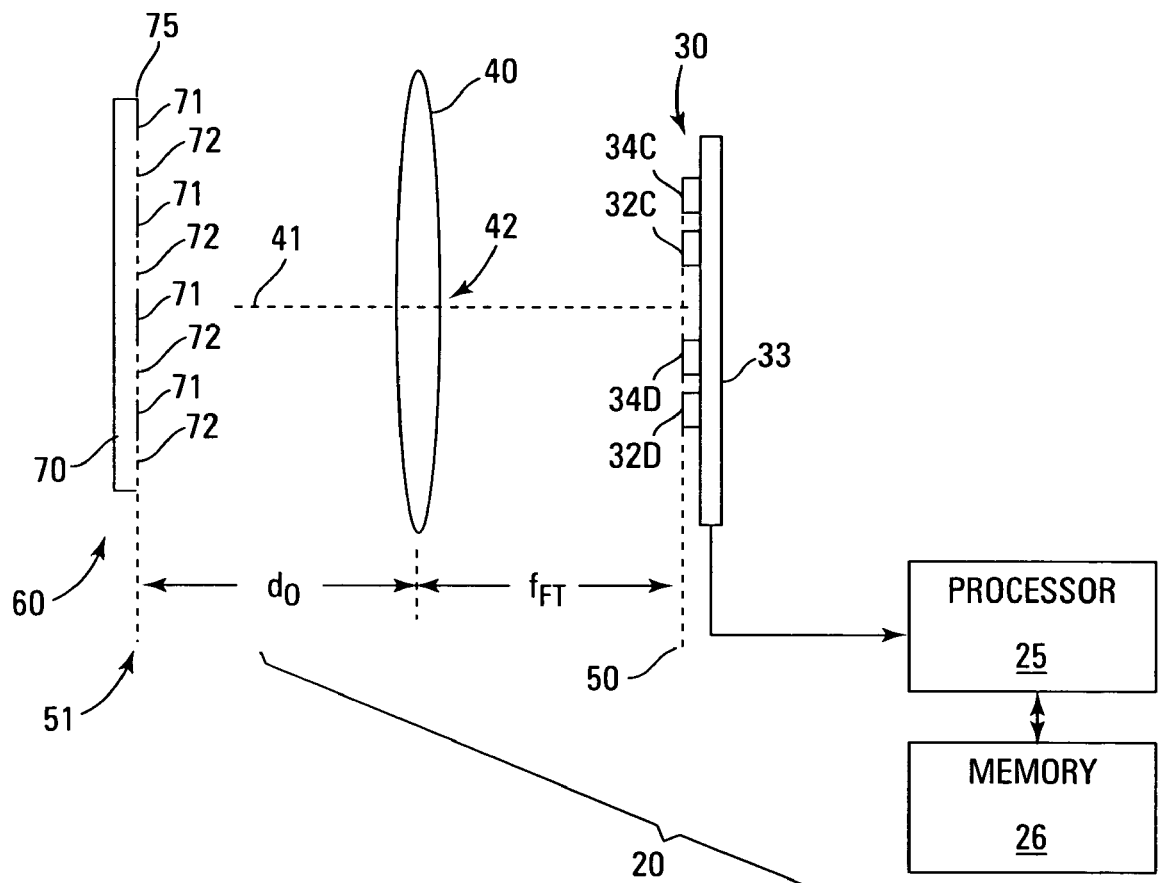

FIGS. 1A and 1B are views of one embodiment of a Fourier transform optical detection system 20 for use with a test assay 60 having a sensitivity pattern 100. The sensitivity pattern 100 is also referred to as a "Fourier transformable pattern 100" since the sensitivity pattern 100 can be Fourier transformed by a lens 40. The sensitivity pattern 100 is segmented into quadrants 100A, 100B, 100C and 100D by the line 98, which vertically bisects the sensitivity pattern 100, and by the line 99, which horizontally bisects the sensitivity pattern 100.

The test assay 60 is also referred to as "assay 60." The Fourier transform optical detection system 20 is also referred to as "detection system 20." The detection system 20 comprises a lens 40 having a Fourier transform plane $f_{FT}$ and a detector array 30. The detector array 30 is segmented into quadrants 30A, 30B, 30C and 30D by the line 28, which vertically bisects the detector array 30, and by the line 29, which horizontally bisects the detector array 30.

The detector array 30 includes first detectors 32A, 32B, 32C and 32D, also referred to here as "first detectors 32" and "first detector 32." The detector array 30 additionally includes second detectors 34A, 34B, 34C, and 34D, also referred to here as "second detectors 34" and "second detector 34." The first detectors 32A, 32B, 32C and 32D are each centered in the respective quadrant 30A, 30B, 30C and 30D of the photodetector array 30. The second detectors 34A, 34B, 34C, and 34D are each in the respective quadrant 30A, 30B, 30C and 30D of the photodetector array 30 in a location offset from the first detectors 32A, 32B, 32C and 32D. The first detectors 32 and the second detectors 34 are all located in the Fourier transform plane $f_{FT}$.

The first detectors 32 and the second detectors 34 are positioned in an arrangement of a Fourier transform pattern of the sensitivity pattern 100 so that the first detectors 32 detect light at peak-intensity regions of the Fourier transform pattern of the sensitivity pattern 100 in the Fourier transform plane 50 (FIG. 1B) and the second detectors 34 detecting light in at least one low-intensity region of the Fourier transform pattern of the sensitivity pattern 100 in the Fourier transform plane 50. The intersection of lines 98 and 99, the center 42 of the lens 40, and the intersection of lines 28 and 29 are all aligned with each other on the optical axis 41 of the lens 40.

The sensitivity pattern 100 is a checkerboard pattern of detection regions represented generally by the numeral 71 and non-detection regions represented generally by the numeral 72 in test assay 60. The detection regions 71 are regions which are able to react to the presence of a test analyte in a test sample, when the test assay 60 is exposed to the test sample having the test analyte. In order to facilitate visualization of the sensitivity pattern 100, the detection regions 71 are darker than the non-detection regions 71 in FIG. 1A. In this embodiment, the sensitivity pattern comprises 100 a uniform array of a pattern. Other patterns are possible.

FIG. 1A is an oblique view of the detection system 20. FIG. 1B is a side view of the detection system 20. The test assay 60 is located at an object distance $d_o$ from the lens 40. The top surface 75 of the assay substrate 70, also referred to as "substrate 70," is in an object plane 51 (FIG. 1B) of the lens 40. The object plane 51 (shown in cross-section in FIG. 1B) is perpendicular to the optical axis 41 of the lens 40.

The detector array 30 is located at a distance $f_{FT}$ from the lens 40 opposing the test assay 60 in the Fourier transform plane 50 (shown in cross-section in FIG. 1B) of the lens 40. The front surface of the detector array 30 is in the Fourier transform plane 50. The Fourier transform of the sensitivity pattern 100 is imaged by the lens 40 in the Fourier transform plane 50.

The detection system 20 also includes a processor 25 communicatively coupled to the detector array 30. The first detector 32 and the second detector 34 each generate signals indicative of the intensity of light incident on the first detector 32 and the second detector 34, respectively. The processor 25 receives the signals and determines if the first detector 32 and the second detector 34 are receiving light in a pattern of a Fourier transform of the sensitivity pattern 100.

The detection system 20 also includes a memory 26 communicatively coupled to the processor 25. At least a portion of software and/or firmware executed by the processor 25 and any related data structures are stored in memory 26.

Figure 2A:
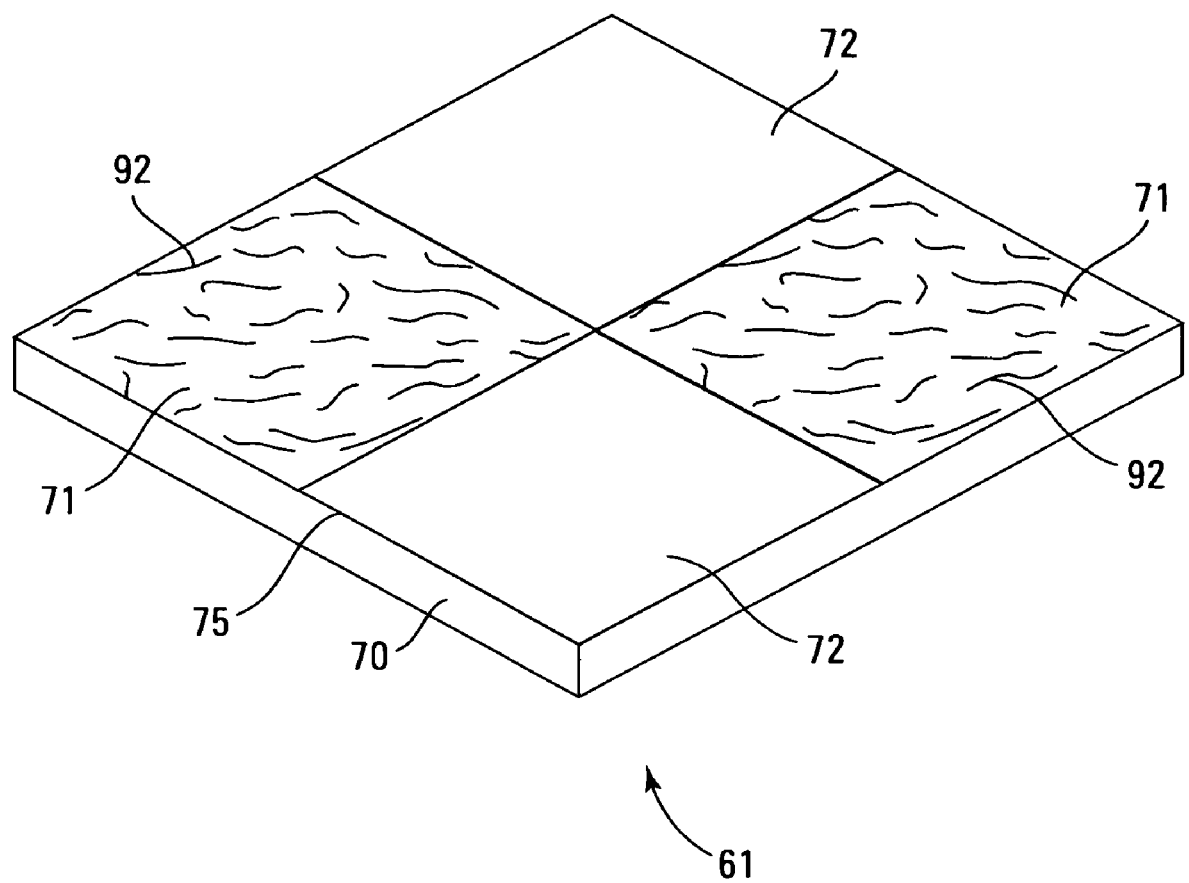
FIGS. 2A and 2B is an enlarged view of a portion of the test assay before and after exposure to a test sample, respectively.
Figure 2B:
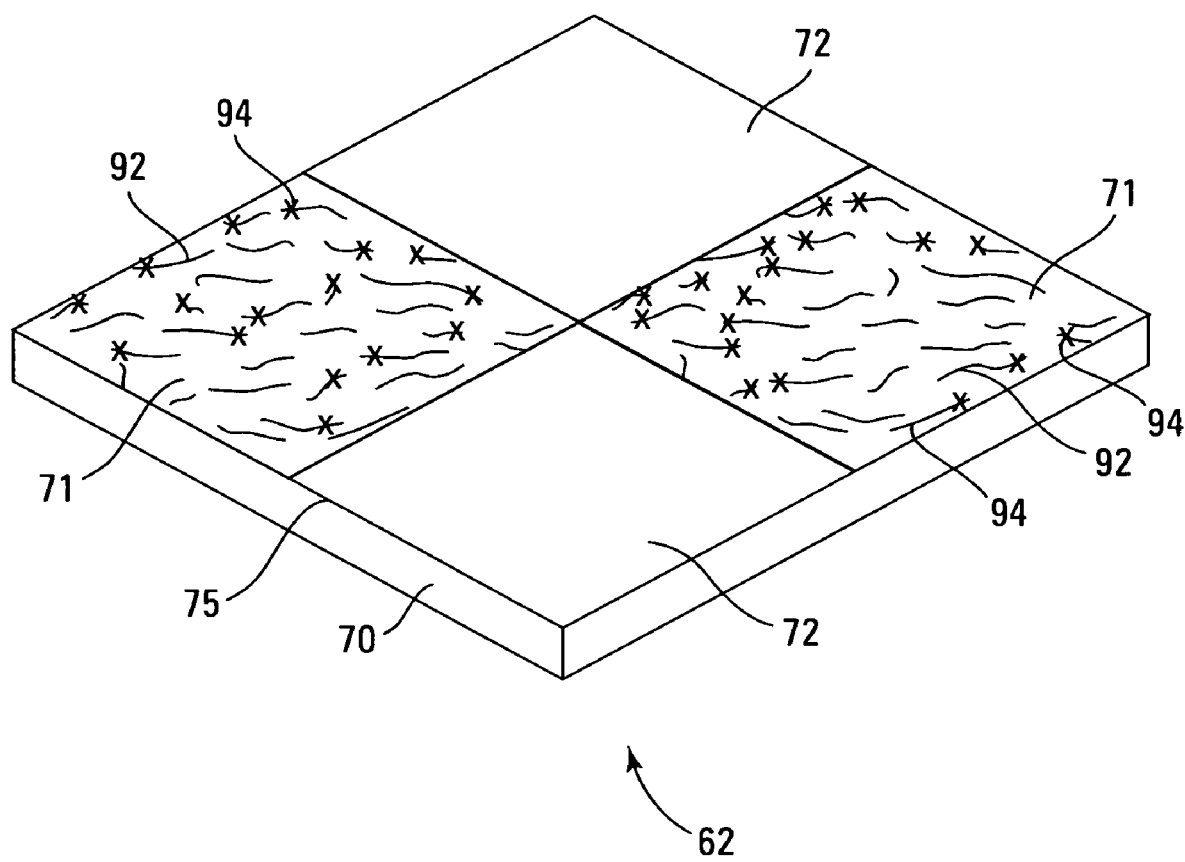

FIGS. 2A and 2B are enlarged views of a portion of the test assay 60 (FIG. 1) before and after exposure to a test sample, respectively. FIG. 2A shows a portion 61 of the test assay 60, which includes two detection regions 71 and two non-detection regions 72, before exposure of reagents (shown as curved lines and generally represented as numeral 92) to a test sample that includes reactive test analytes. FIG. 2B is an enlarged view a portion 62, which includes two detection regions 71 and two non-detection regions 72, of the test assay 60 (FIG. 1) after exposure to the test sample that includes reactive test analytes, also referred to as "test analytes 94," shown as X's, and represented generally by the numeral 94. The test analytes 94 are bonded to the reagents 92 in the detection regions 71. The detection regions 71 include the reagents 92 attached to the top surface 75 of the substrate 70. The reagents 92 in detection regions 71 are able to bond to a reactive test analyte 94 when the test analytes 94 come into contact with the reagents 92. The non-detection regions 72 do not have any attached reagents 92.

The reagents 92 in the detection regions 71 react with the test analyte 94 such that the optical characteristics of the surface are changed and light is emitted, reflected or transmitted in the Fourier transformable pattern 100 (FIG. 1). In one implementation of this embodiment, the reagents 92 in the detection regions 71 bond to the test analyte 94 and the bonded material emits light from the detection regions 71. In another implementation of this embodiment, gold atoms are attached to the test analyte 94 and the bonding of the reagents 92 to the test analyte 94 is detected as reflected light when light is incident on the test assay 60. In yet another implementation of this embodiment, if a reaction has occurred, the bonded reagents 92 and test analytes 94 fluoresce upon exposure to the incident light. In another implementation of this embodiment, each test analyte 94 includes an attached fluorescent molecule. The Fourier transformable pattern 100 has at least one intensity peak with a contrast greater than 0.5 when Fourier transformed by lens 40 (FIG. 1).

Figure 3A:
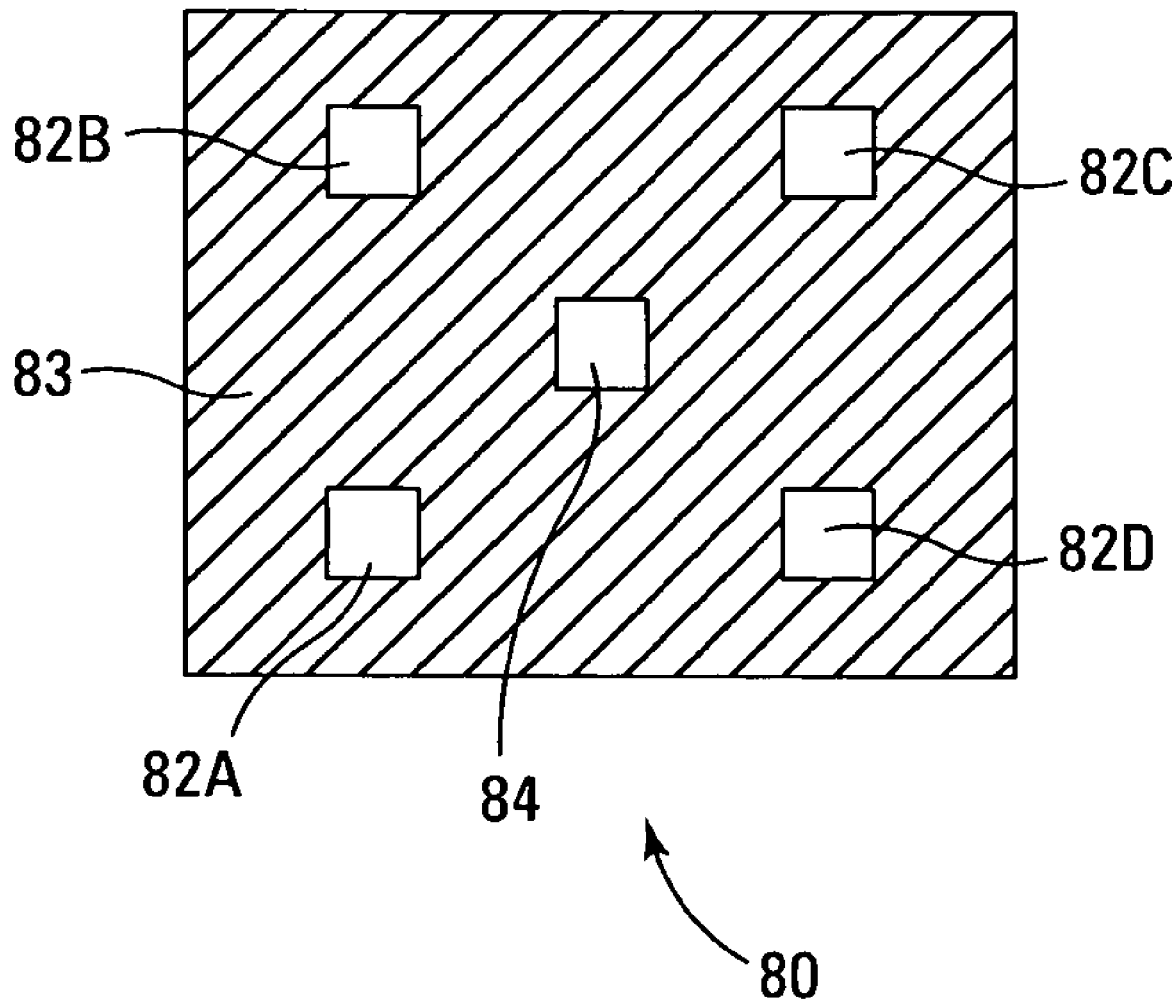
FIG. 3A is a Fourier transform of the sensitivity pattern.

FIG. 3A is a Fourier transform pattern 80 of the sensitivity pattern 100 (FIG. 1A). The Fourier transform pattern 80 is shown as viewed from the position of the lens 40 in FIG. 1A. After the test assay 60 is exposed to a test sample (not shown) that includes reactive test analyte 94, light is emitted, transmitted or reflected from the top surface 75 of the test assay 60 in the pattern of the sensitivity pattern 100. The light emitted, transmitted or reflected from the top surface 75 (FIG. 1B) of the test assay 60 is transmitted through the lens 40. The light transmitted through the lens 40 is Fourier transformed by the lens 40 and focused in the resulting Fourier transform pattern 80 at the Fourier transform plane 55 located the distance $f_{FT}$ from the lens 40 (FIGS. 1A and 1B). Since the sensitivity pattern 100 is a checkerboard, two dimensionally shaped peak-intensity regions (represented as white squares labeled with numerals 82A, 82B, 82C, and 82D in a crosshatch background) are imaged in the Fourier transform plane 50 (FIG. 1B). The two dimensionally shaped peak-intensity regions 82A, 82B, 82C, and 82D are also referred to here as "peak-intensity regions 82." At the peak-intensity regions 82, a peak intensity of light is incident on the first detectors 32 (FIGS. 1A and 1B) located in the Fourier transform plane 50.

When the Fourier transform pattern 80 is imaged on the photodetector array 30 in FIG. 1A, the second detectors 34 are positioned in a low-intensity region of the Fourier transform pattern 80 of the sensitivity pattern 100. The low-intensity region is represented generally by the numeral 83 and indicated by the cross hatching. The low-intensity region 83 includes all of the Fourier transform pattern 80 outside of the peak-intensity regions 82 and the average signal region 84 referred to here as the "DC-component region 84." The second detectors 34 can be placed anywhere in the low-intensity region 83 of the Fourier transform pattern 80.

The intensity of light at the peak-intensity regions 82, referred to here as $I_{peak}$, is much higher than the intensity of the light at the low-intensity region 83, referred to here as $I_{low}$, therefore the Fourier transformable pattern 100, when Fourier transformed, has at least one high contrast peak at peak-intensity regions 82. The peak-intensity regions 82 are intensity peaks in the Fourier transformed pattern with a contrast greater than 0.5. The contrast of the Fourier transform pattern 80 is defined here as $(I_{peak}-I_{low})/(I_{peak}+I_{low})$. In one implementation of this embodiment, the peak-intensity regions 82 are intensity peaks in the Fourier transformed pattern with a contrast that is discernable by the human eye.

The optical axis 40 (FIGS. 1A and 1B) intersects the Fourier transform plane 50 at the average signal region 84. The DC-component region 84 is a two dimensionally shaped light pattern (shown as a square white box) located in the center of the Fourier transform pattern 80 in the Fourier transform plane 50 (FIG. 1B). The DC-component region 84 has an intensity level that correlates to the mean intensity of the contrast between the intensity of light from the detection region 71 and the non-detection region 72. If the average light intensity emitted, transmitted or reflected from the top surface 75 of the test assay 60 from the detection region 71 is $I_{hi}$ and the average light intensity emitted, transmitted or reflected from the non-detection region 72 is $I_{low}$, the intensity of light in the DC-component region 84 is proportional to $(I_{hi}+I_{low})/2$.

In this manner as shown in FIGS. 1A, 1B, 2A, 2B and 3A, the first detectors 32 and the second detectors 34 of detector array 30 are positioned in an arrangement of a Fourier transform pattern 80 of the sensitivity pattern 100. Specifically, the first detector 32A is located to detect light in the peak-intensity region 82A, the first detector 32B is located to detect light in the peak-intensity region 82B, the first detector 32C is located to detect light in the peak-intensity region 82C, and the first detector 32D is located to detect light in the peak-intensity region 82D. Likewise, the second detector 34A is located to detect light in the low-intensity region 83 that is offset from the peak-intensity region 82A, the second detector 34B is located to detect light in the low-intensity region 83 that is offset from the peak-intensity region 82B, the second detector 34C is located to detect light in the low-intensity region 83 that is offset from the peak-intensity region 82C, and the second detector 34D is located to detect light in the low-intensity region 83 that is offset from the peak-intensity region 82D.

In one implementation of this embodiment, the Fourier transform optical detection system 20 includes only one second detector 34A, 34B, 34C or 34D that detects the light level in the low-intensity region 83 and only one first detector 32A, 32B, 32C or 32D that detects the light level in the respective peak-intensity region 82A, 82B, 82C, or 82D.

The first detectors 32 and the second detectors 34 do not need to be high resolution detectors. The first detectors 32 and the second detectors 34 do not need to be positioned as closely to each other as the detection regions 71 are positioned to each other on the test assay 60, since the detector array 30 is not resolving the image of the light emitted, transmitted or reflected from the test assay 60 in the sensitivity pattern 100. In one implementation of this embodiment, the first detectors 32 and the second detectors 34 are large area semiconductor photodetectors. The detection system 20 (FIGS. 1A and 1B) includes first detectors 32 and the second detectors 34 that are operable to detect the wavelength of the light emitted, transmitted or reflected from the test assay 60.

Figure 3B:
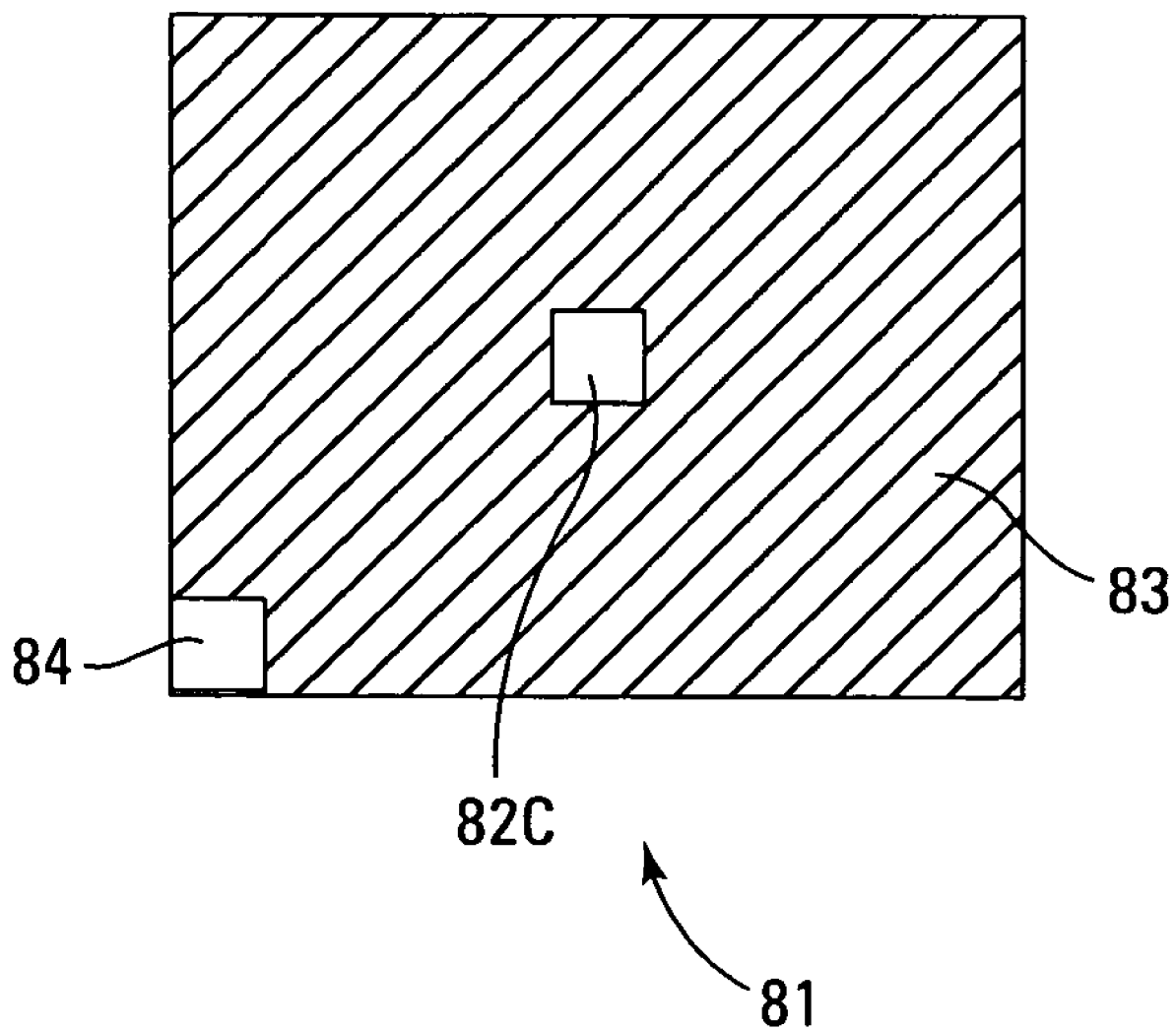
FIG. 3B is an upper-right hand quadrant of the Fourier transform pattern of FIG. 3A.

FIG. 3B is an upper-right hand quadrant 81 of the Fourier transform pattern 80 of FIG. 3A. The upper-right hand quadrant 81 is also referred to here as "quadrant 81." The DC-component region 84 is now in the lower-left hand corner of the Fourier transform pattern and the peak-intensity region 82C is centered in the quadrant 81. Likewise, the peak-intensity regions 82A, 82B and 82D are centered in their respective quadrants of the Fourier transform pattern 80. The discussion related to FIGS. 5A-5D is based on a software modeling of quadrant 81 of the Fourier transform pattern 80.

Figure 4:
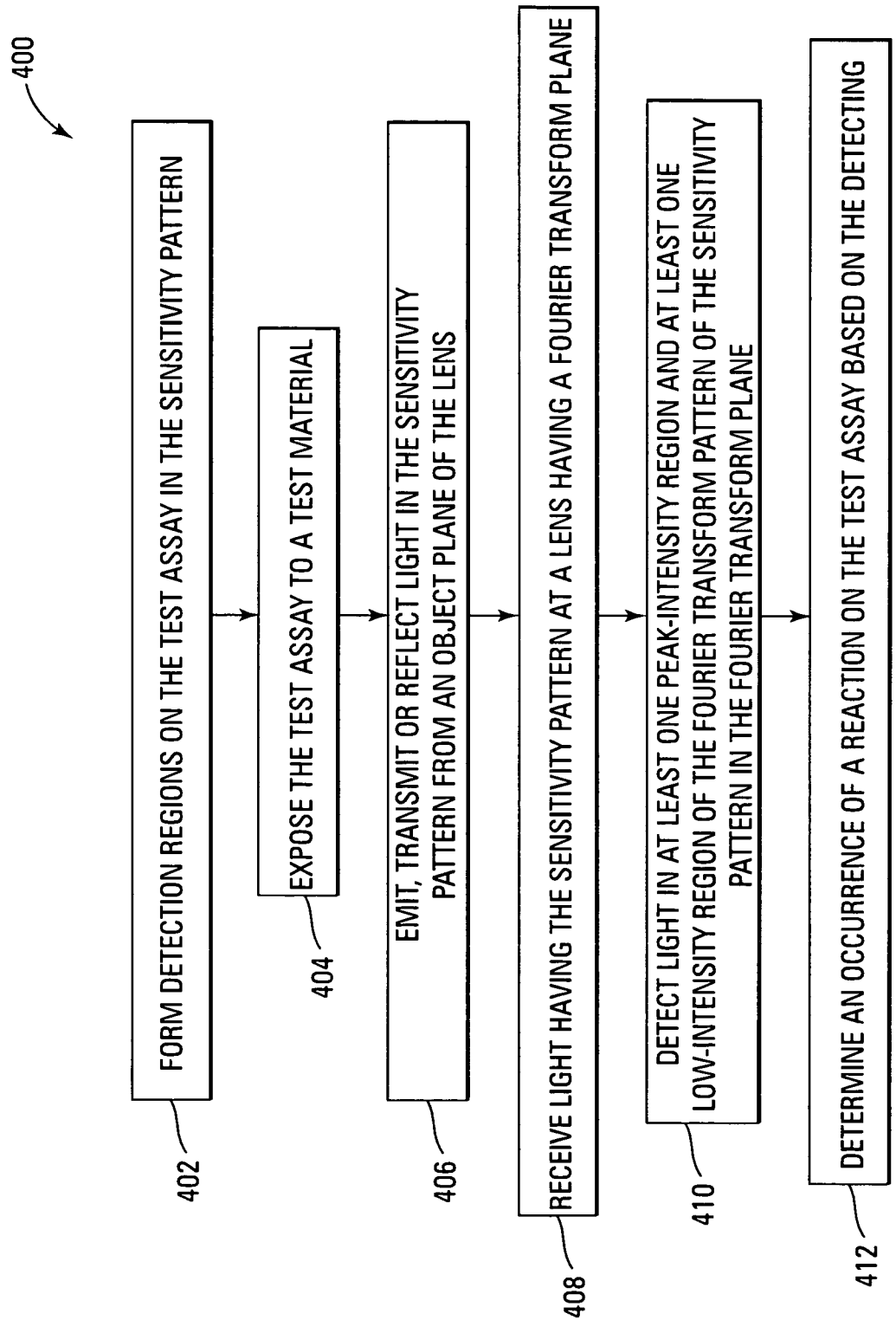
FIG. 4 is a flow diagram of one embodiment of a method to increase a signal to noise ratio during a measurement of a test assay using the Fourier transform detection system.

FIG. 4 is a flow diagram of one embodiment of a method 400 to increase the signal to noise ratio SNR during a measurement of a test assay 60 using the Fourier transform detection system 20. The particular embodiment of method 400 shown in FIG. 4 is described here as being implemented for use with the detection system 20 described above in connection with FIGS. 1A, 1B, 2A, 2B and 3B. Other embodiments are possible.

At block 402, the detection regions 71 are formed on the test assay 60 in the sensitivity pattern 100. In one implementation of this embodiment, detection regions 71 are formed by patterning the substrate 70 to expose all the detection regions 71 shown in FIG. 1A and then attaching the reagent 92 to exposed detection regions 71 of the substrate 70. The methods of attaching the reagent 92 are set by the type of substrate 70 and by the type of reagent 92. The detection regions 71 are operable to react to a test analyte 94 so the test assay 60 emits, transmits or reflects light in the sensitivity pattern 100. In one implementation of this embodiment, more than one type of reagent is attached to the exposed areas of the substrate 70.

At block 404, the test assay 60 is exposed to a test material that includes reactive test analyte 94. The test analyte 94 and the reagent 92 bond to each other when they come into contact. In one implementation of this embodiment, a test sample including test analyte 94 is washed over the top surface 75 of the test assay 60 in order to expose the test assay 60 to the test analyte 94. In another implementation of this embodiment, the test assay 60 is dipped into the test sample including test analyte 94, in order to expose the test assay 60 to the test analyte 94. In another implementation of this embodiment, capillary forces are implemented in channels on the test assay 60 in order to expose the test assay 60 to the test analyte 94. Other exposure techniques are possible.

At block 406, light is emitted, transmitted or reflected from the test assay 60 in the sensitivity pattern 100 from the object plane 51 of the lens 40. In one implementation of this embodiment, the bonded reagents 92 and test analytes 94 emit light of a first wavelength when an external light of a second wavelength is incident on the test assay 60. In another implementation of this embodiment, the bonded reagents 92 and test analytes 94 spontaneously emit light after the reagents 92 and test analytes 94 bond to each other.

At block 408, the lens 40 lens having a Fourier transform plane 50 receives the light having the sensitivity pattern 100. The lens 40 is positioned an object distance $d_o$ from the top surface 75 of the test assay 60 so that the optical axis 41 is perpendicular to the top surface 75 of the substrate 70 (FIG. 1B).

At block 410, the detector array 30 detects light from least one peak-intensity region 82 and at least one low-intensity region 83 of the Fourier transform pattern 80 (FIG. 3A) of the sensitivity pattern 100 in the Fourier transform plane 50. For example, the first detector 32C (FIG. 1A) is located at the peak intensity 82C (FIG. 3B) of the quadrant 81 of the Fourier transform pattern 80. The second detector 34C (FIG. 1A) is located away from the peak intensity 82C in the low-intensity region 83 (FIG. 3B) of the quadrant 81 of the Fourier transform pattern 80.

At block 412, the processor 25 determines an occurrence of a reaction on the test assay 60 based on the detecting during block 410. If light is detected by first detectors 32 and little or no light is detected by second detectors 34, the processor 25 determines that the first detectors 32 are receiving light from the peak-intensity regions 82 of the sensitivity pattern 100 and the test analyte 94 is attached to the reagent 92 in the detection regions 71 of the test assay 60.

If similar low light levels are detected by the first detectors 32 and the second detectors 34, the processor 25 determines that the first detectors 32 are not receiving peak intensity light where the peak-intensity regions 82 of the sensitivity pattern 100 is expected and that the test analyte 94 is not attached to the reagent 92 in the detection regions 71 of the test assay 60.

In one implementation of this embodiment, the detector array 30 is operable to detect more than one Fourier transform pattern. In this case, the processor 25 receives input indicative of the sensitivity pattern of the test assay 60 positioned in the object plane 51 of the lens 40 in detection system 20. The processor 25 evaluates the signals from the set of detectors or photodetector elements in a photodetector array that are needed to determine if the sensitivity pattern of interest is in the object plane 51 of the lens 40. When a new test assay 60 with a different sensitivity pattern is placed in the object plane 51 of the lens 40 in detection system 20, the processor 25 receives input indicative of the sensitivity pattern of the new test assay 60 and evaluates signals from a new set of detectors in the detector array 30 or photodetector elements in a photodetector array.

The processor 25 executes software and/or firmware that causes the processor 25 to determine if a reaction occurred between the test analyte 94 and the reagent 92. At least a portion of such software and/or firmware executed by the processor 25 and any related data structures are stored in memory 26 during execution. Memory 26 comprises any suitable memory now known or later developed such as, for example, random access memory (RAM), read only memory (ROM), and/or registers within the processor 25. In one implementation, the processor 25 comprises a microprocessor or microcontroller. Moreover, although the processor 25 and memory 26 are shown as separate elements in FIG. 1, in one implementation, the processor 25 and memory 26 are implemented in a single device (for example, a single integrated-circuit device). The software and/or firmware executed by the processor 25 comprises a plurality of program instructions that are stored or otherwise embodied on the memory 26 or another storage medium from which at least a portion of such program instructions are read for execution by the processor 25. In one implementation, the processor 25 comprises processor support chips and/or system support chips such as ASICs.

The detection system 20 determines an occurrence of a reaction on the test assay 60 even if the sensitivity pattern 100 has a small intensity variation between the light emitted, transmitted or reflected from the detection regions 71 and the light emitted, transmitted or reflected from the non-detection regions 72. The Fourier transform of a well-chosen sensitivity pattern has relatively high intensity variation (between the peak-intensity region and the low-intensity region) with respect to the intensity variation of the sensitivity pattern (between the detection regions and the non-detection regions).

Figure 5A:
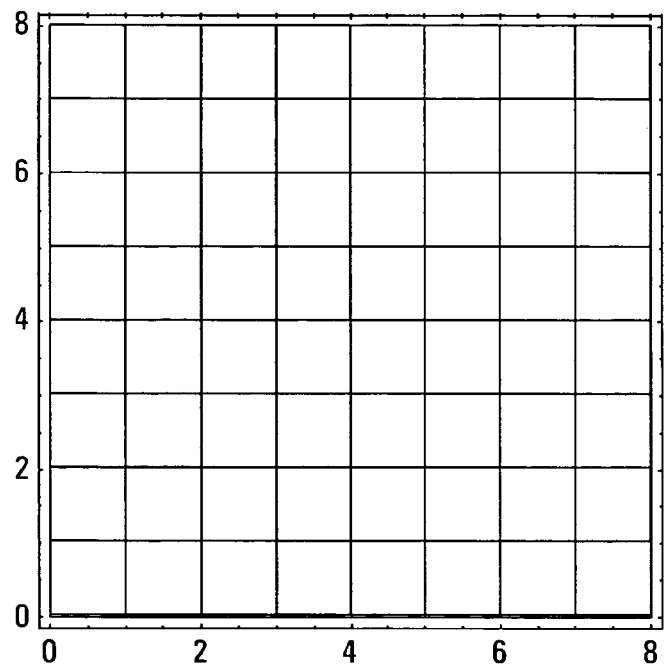
FIGS. 5A-5D show patterns for paired sensitivity patterns and the resultant Fourier transform patterns in which the sensitivity patterns have various intensity variations and noise levels.
Figure 5B:
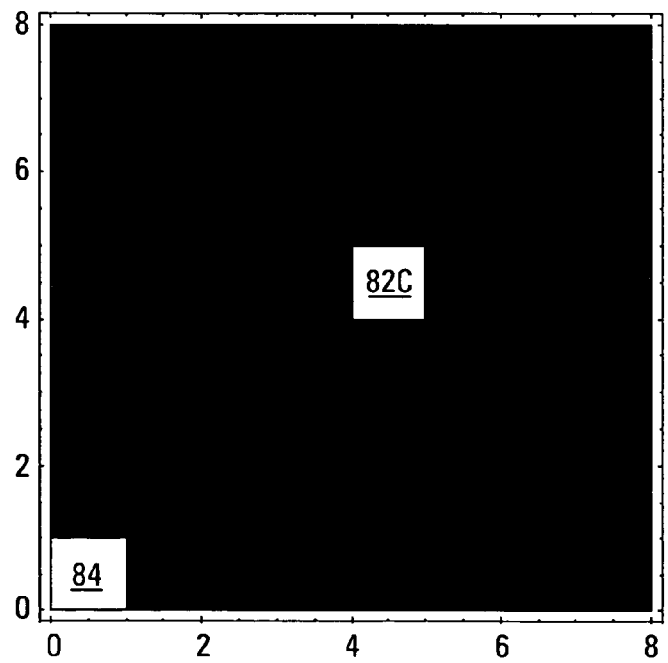
Figure 5C:
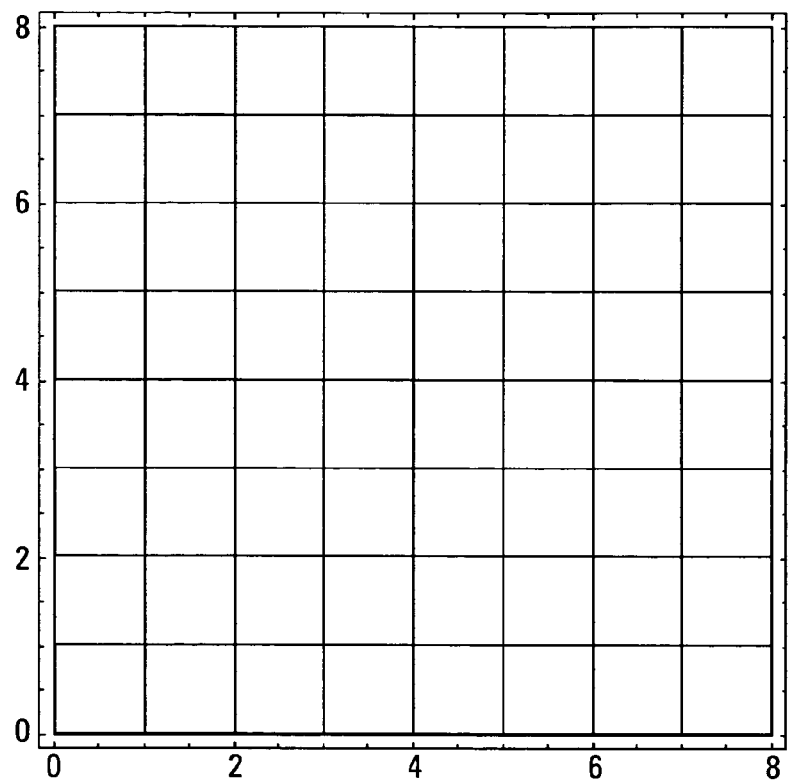

A human observer has difficulty seeing a 2% intensity variation in the checkerboard pattern as is shown in FIG. 5C. In some cases, a human observer has difficulty seeing a 10% intensity variation in the checkerboard pattern. In order to illustrate that the Fourier transform of a sensitivity pattern has a relatively high intensity variation with respect to the intensity variation of the sensitivity pattern, FIGS. 5A-5D show patterns for paired sensitivity patterns and the resultant Fourier transform patterns in which the sensitivity patterns 100 have various intensity variations and noise levels.

FIG. 5A is a portion of a sensitivity pattern 102 exemplary of a modeled sensitivity pattern having about a 10% intensity variation between the detection regions 71 and non-detection regions 72 and +/−1.5% uniform random noise. Thus, each of the detection regions 71 and the non-detection regions 72 in the test assay 60 emit, transmit or reflect an intensity of light that can vary in a random uniform manner by ±1.5%. FIG. 5B is a quadrant 182 of the modeled Fourier transform pattern of the modeled sensitivity pattern 102 of FIG. 5A. The complete Fourier transform pattern is similar to the Fourier transform pattern 80 of FIG. 3A. The intensity ratio between the peak-intensity region 82C and the low-intensity region 83 (FIG. 3A) is about 20/1.

In FIG. 5A, the checkerboard pattern is a schematic representation of the modeled checkerboard pattern having about a 10% intensity variation between the detection regions 71 and non-detection regions 72 and +/−1.5% non-uniform random noise. In the modeling for the sensitivity pattern 102 of FIG. 5A, the intensity of light from the detection regions 71 is 100±1.5 and the intensity of light from non-detection regions 72 is about 90±1.5 for an intensity ratio of about 100/90=1.11. Specifically for the modeled sensitivity pattern in FIG. 5A, the intensity ratio ranges from about 101.5/88.5=1.15 to about 98.5/91.5=1.07.

The Fourier transform optical detection system 20 (FIGS. 1A and 1B) detects the 20/1 intensity ratio of the Fourier transformed sensitivity pattern 102 with first detectors 32 and at least one of the second detectors 34 in the Fourier transform pattern in Fourier transform plane 50 (FIG. 1B) of the lens 40. For example, the two detectors 32C and 34C detect light in the quadrant 182 of the Fourier transform pattern in Fourier transform plane 50 (FIG. 1B) of the lens 40 and the other first detectors 32 detect light in the other quadrants of the Fourier transform pattern. In one implementation of this embodiment, only the two detectors 32C and 34C are included in the photodetector array 30 to detect light in the Fourier transform pattern 80 in Fourier transform plane 50 (FIG. 1B) of the lens 40. Thus, the Fourier transform optical detection system 20 is simpler than an optical detection system needed to detect a checkerboard pattern having 10% intensity variation that is imaged in an image plane of a lens.

In FIG. 5C, the checkerboard pattern is a schematic representation of a portion of the modeled checkerboard pattern having about a 2% intensity variation between the detection regions 71 and non-detection regions 72 and +/−1.5% non-uniform random noise. In FIG. 5C, the intensity of light from the detection regions 71 is 100±1.5 and the intensity of light from non-detection regions 72 is about 98±1.5 for an intensity ratio of about 100/98=1.02.

Figure 5D:
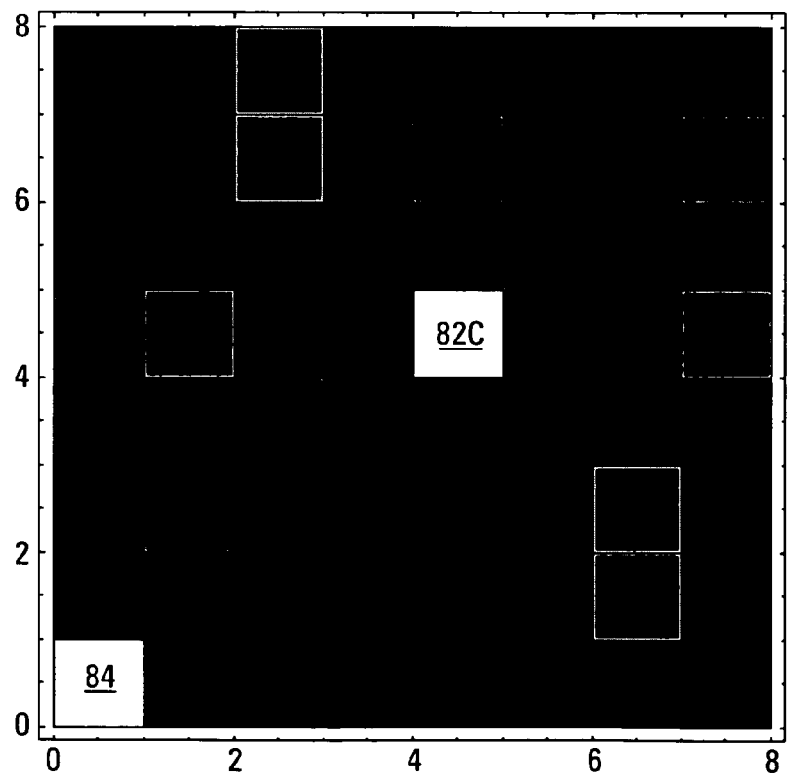

FIG. 5D is a quadrant 183 of the modeled Fourier transform pattern of the modeled sensitivity pattern 103 of FIG. 5C. The complete Fourier transform pattern of sensitivity pattern 103 is similar to the Fourier transform pattern 80 of FIG. 3A. In FIG. 5D, the smallest intensity ratio between the peak-intensity region 82C and the low-intensity region 83 (FIG. 3A) is about 3/1.

A Fourier transform optical detection system, such as the system 20 described above with reference to FIGS. 1A and 1B, is able detect the intensity ratio of FIG. 5D with two detectors in the quadrant 183 of the Fourier transform plane 50. Thus, the low cost detection system 20 is able to determine the occurrence of a reaction between the test analyte 94 and the regent 92 for this low contrast sensitivity pattern, such as sensitivity pattern 103 of FIG. 5C, using between 2 to 8 low cost large area detectors and a processor 25 that determines a ratio between the light levels in the two detectors 32 and 34. The human eye could not distinguish the sensitivity pattern 100 at 2% intensity variation with certainty.

Figure 6:
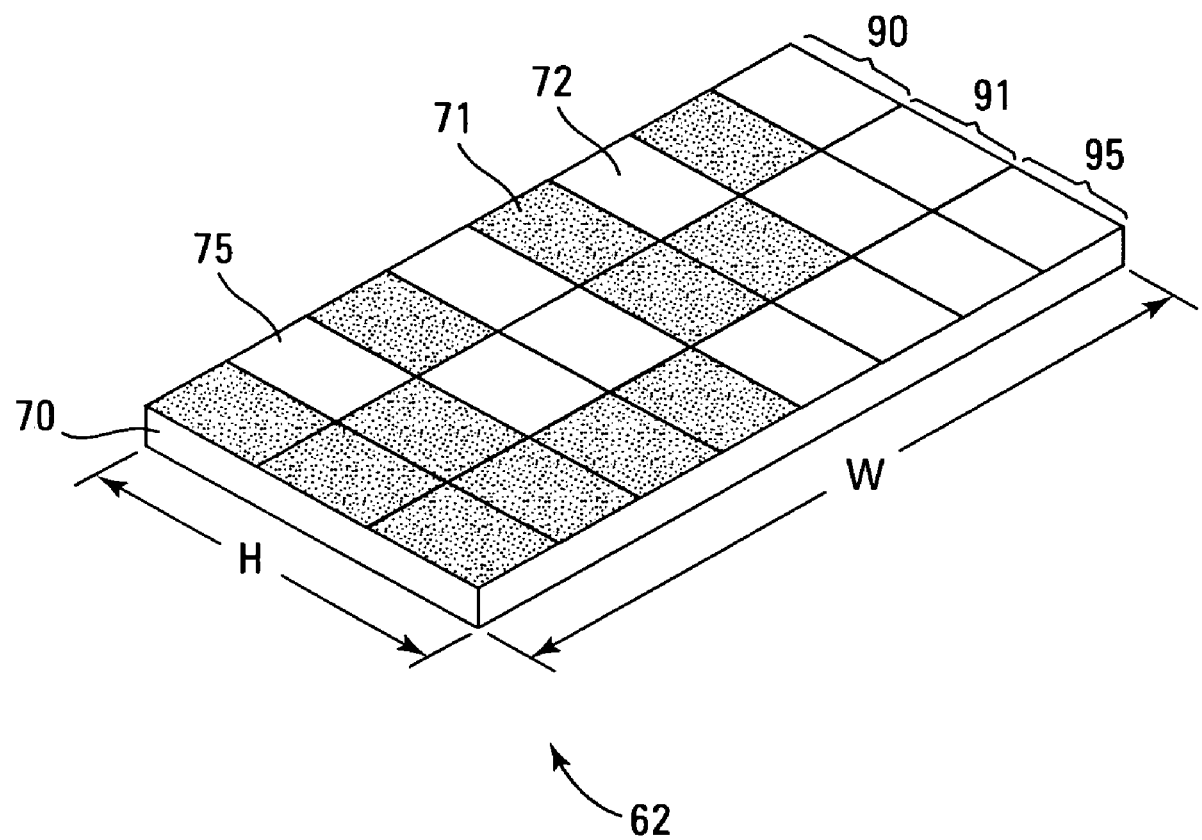
FIG. 6 is an oblique view of one embodiment of a test assay having many sensitivity patterns on a surface of a substrate.

Other sensitivity patterns having least one high contrast peak when Fourier transformed by a lens 40 or lens system are possible. FIG. 6 is an oblique view of one embodiment of a test assay 62 having three sensitivity patterns on the top surface 75 of the substrate 70. The test assay 62 shown in FIG. 6 includes sensitivity patterns represented generally by the numerals 90, 91 and 95. When the test assay 62 replaces test assay 60 in the system 20, each sensitivity pattern 90, 91 and 95 has a different Fourier transform pattern in the Fourier transform plane 55 (FIG. 1B). In one implementation of this embodiment, the detection regions 71 in each of the sensitivity patterns 90, 91 and 95 react to different test analytes 94. In order to detect the presence of various test analytes, a photo-detector array is designed with at least one detector in a high-intensity region of the Fourier transform pattern of the respective sensitivity pattern and with at least one detector in a low-intensity region of the Fourier transform pattern of the respective sensitivity pattern. The processor determines if each of the various test analytes are present.

Sensitivity pattern 90 includes four detection regions 71 that are alternating with four non-detection regions 72 in a row along the width dimension W. Thus, when the reagents 92 in the detection regions 71 in the sensitivity pattern 90 are bonded with the test analyte 94 (FIG. 2B), the sensitivity pattern 90 emits, transmits or reflects light as a spatial filter having a spatial frequency in one dimension. As used herein, a row forms a spatial filter in one dimension. A matrix such as the sensitivity pattern 100 forms a spatial filter in two dimensions. Also, two rows form a spatial filter in two dimensions. In one implementation of this embodiment, the sensitivity pattern 90 includes detection regions 71 that bond to a first test analyte (not shown).

Sensitivity pattern 91 includes four detection regions 71 that are the same size as the detection regions 71 of sensitivity pattern 90. The four detection regions 71 alternate two by two with four non-detection regions 72 in a row along the width dimension W. Sensitivity pattern 91 is offset in the height dimension H from the sensitivity pattern 90. Thus, when the detection regions 71 in the sensitivity pattern 90 are bonded with the test analyte 94 (FIG. 2B), the sensitivity pattern 90 emits light as a spatial filter having a spatial frequency in one dimension that is half the spatial frequency in one dimension as that in sensitivity pattern 90. In one implementation of this embodiment, the sensitivity pattern 91 includes detection regions 71 that bond to a second test analyte (not shown).

Sensitivity pattern 95 includes detection regions 71 that are the same size as the detection regions 71 of sensitivity pattern 90 and 91. Sensitivity pattern 95 is offset in the height dimension H from the sensitivity pattern 91. Sensitivity pattern 95 includes detection regions 71 that are alternating four by four in the dimension along the width W of the substrate 70 with non-detection regions 72 so the rows have the one fourth the spatial frequency of sensitivity pattern 90 in the dimension along the width W of the substrate 70. In one implementation of this embodiment, the sensitivity pattern 95 includes detection regions 71 that bond to a third test analyte.

As known in the art, many other appropriate sensitivity patterns are possible in one or two dimensions. Specifically, the sensitivity patterns can be in the form of a spatial filter having a spatial frequency in one dimension, multiples of the spatial frequency in one dimension, submultiples of the spatial frequency in one dimension, the spatial frequency in two dimensions, multiples of the spatial frequency in two dimensions, submultiples of the spatial frequency in two dimensions, and combinations thereof. In one implementation of this embodiment, the sensitivity pattern 90, the sensitivity pattern 91 and/or the sensitivity pattern 95 are in two dimensions, that is in two or more rows.

Figure 7:
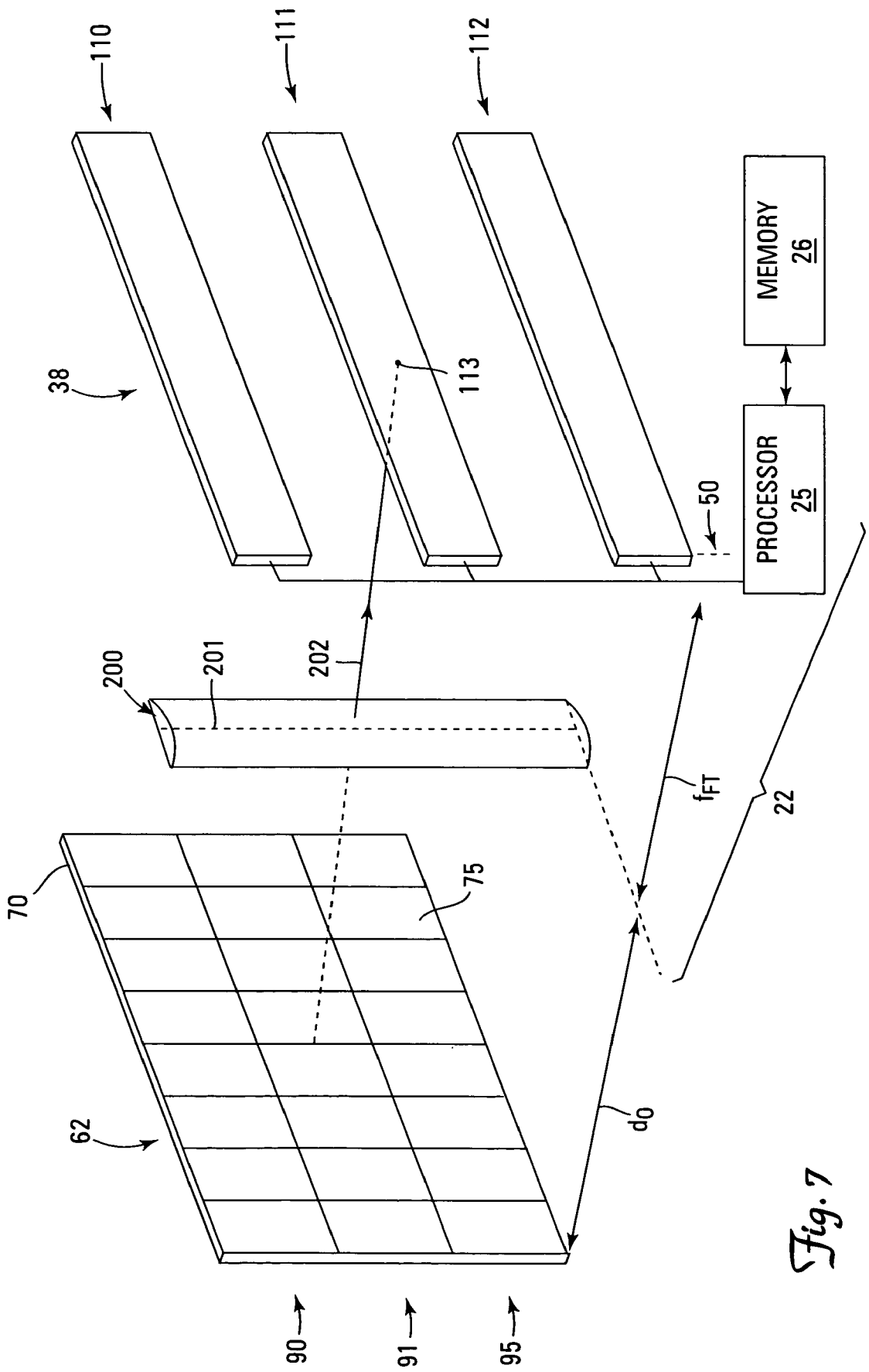
FIG. 7 is an oblique view of one embodiment of a Fourier transform optical detection system for use with a test assay having many sensitivity patterns on a surface of a substrate.

FIG. 7 is an oblique view of one embodiment of a Fourier transform optical detection system 22 for use with the test assay 62 having many sensitivity patterns 90, 91 and 95 on a top surface 75 of a substrate 70 as described above with reference to FIG. 6. The many sensitivity patterns 90, 91 and 95 are also referred to as a "Fourier transformable patterns 90, 91 and 95." The test assay 62 is also referred to as "assay 62." The Fourier transform optical detection system 22 is also referred to as "detection system 22." The test assay 62 was described above with reference to FIG. 6.

The detection system 22 comprises a cylindrical lens 200, a detector array represented generally by the numeral 38, a processor 25 and a memory 26. The detector array 38 includes a first linear detector array 110, a second linear detector array 111 and a third linear detector array 112, all located in the Fourier transform plane $f_{FT}$. Each of the first linear detector array 110, the second linear detector array 111 and the third linear detector array 112 include at least two detectors. All the detectors in the first linear detector array 110, the second linear detector array 111 and the third linear detector array 112 together are positioned in an arrangement of a Fourier transform pattern of the many sensitivity patterns 90, 91 and 95. The detectors in the first linear detector array 110, the second linear detector array 111 and the third linear detector array 112 are communicatively coupled to the processor 25.

The cylindrical lens 200 has a Fourier transform plane $f_{FT}$. The cylindrical lens 200 has a cylindrical axis 201 and an optical axis 202. The optical axis 202 is positioned to be perpendicular to the top surface 75 of the test assay 62 and perpendicular to the Fourier transform plane (distinguished at an edge of the plane as dashed line 50) in which the detector array 38 is positioned. The front faces of the first linear detector array 110, the second linear detector array 111 and the third linear detector array 112 are all positioned in the Fourier transform plane 50. The optical axis 202 is aligned to the center of the top surface 75 of the test assay 62 and the point 113 in the second linear array 111 in the detector array 38. The cylindrical axis 201 is perpendicular to the optical axis 202 and is parallel to the height dimension H of the test assay 62 (FIG. 6). The cylindrical axis 201 and the optical axis 202 lie in a plane that is perpendicular to the top surface 75 of the test assay 62 and perpendicular to the Fourier transform plane 50.

In one implementation of this embodiment, the first linear detector array 110, the second linear detector array 111 and the third linear detector array 112 are each an electronic imaging device, such as a charge-coupled device (CCD) systems or a CMOS-based system. In another implementation of this embodiment, the first linear detector array 110, the second linear detector array 111 and the third linear detector array 112 are a single electronic imaging device, such as a charge-coupled device (CCD) systems or a CMOS-based system.

The processor 25 determines the presence of any test analytes that bond to the test assay 62 as described above with reference to method 400 of FIG. 3. The processor 25 is communicatively coupled to the memory 26.

The detectors comprise linear arrays of detectors, a two dimensional array of detectors, imaging devices having arrays of pixels, detectors having one size, detectors having various sizes, and combinations thereof. The lens systems comprise a cylindrical lens, a spherical lens, an array of cylindrical lenses, an array of spherical lenses, and combinations thereof.

Figure 8:
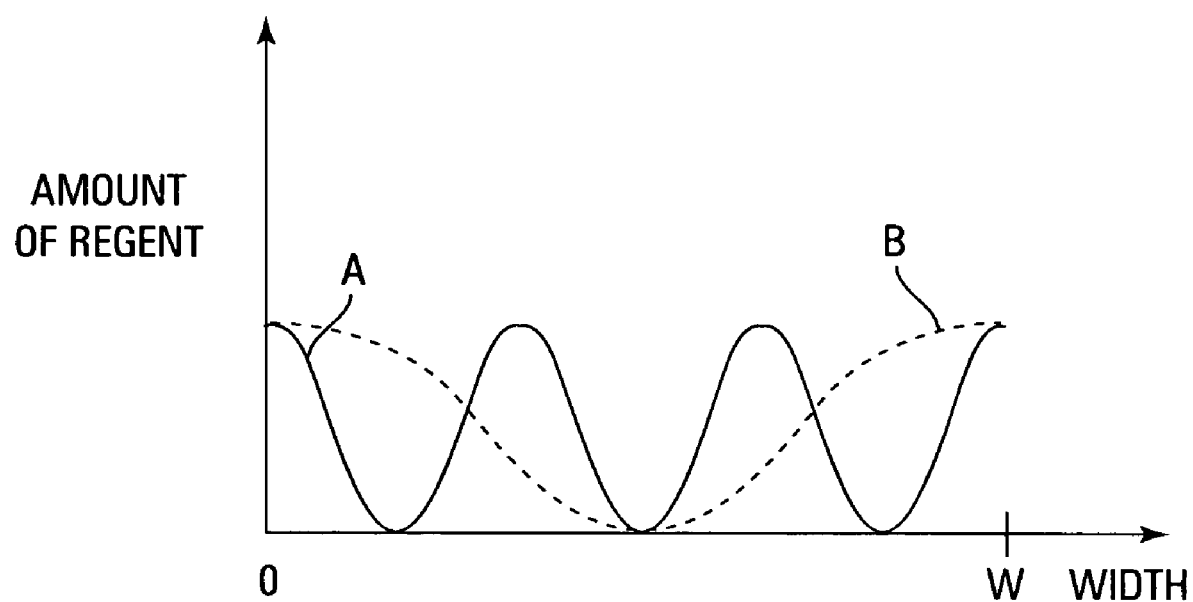
FIG. 8 shows plots of amounts of reagent versus a width of a substrate.

In one implementation of this embodiment, the sensitivity pattern comprises a sinusoidal pattern in one dimension or two dimensions. FIG. 8 shows plots of amounts of reagent versus a width of a substrate 70 (FIG. 6). By varying the amount of reagent in a sinusoidal manner, the intensity of light emitted from the reagent after it bonds to a test analyte varies in the same sinusoidal pattern. In an exemplary case, a first sinusoidal sensitivity pattern is located at a first region of the test assay (for example, the first sinusoidal sensitivity pattern replaces the sensitivity pattern 90 in FIG. 6 so that the first region is the first row along dimension W of the test assay 62 in FIG. 6). The first sinusoidal sensitivity pattern includes a first reagent is in an amount that varies sinusoidally at a first frequency 3/W as represented by the solid sinusoidal curve indicated with the label A.

In one implementation of this embodiment, a second sensitivity pattern is also located at the first region of the test assay. In this exemplary case, the second sinusoidal sensitivity pattern and the second sinusoidal sensitivity pattern replace the sensitivity pattern 90. The second sinusoidal sensitivity pattern includes a second reagent in an amount that varies sinusoidally at a second frequency of 2/W as represented by the dashed sinusoidal curve indicated with the label B. In this manner, the first sensitivity pattern varies sinusoidally at the first frequency 3/W and detects the presence of the first test analyte located at the first region of the test assay while the second sensitivity pattern varies sinusoidally at the second frequency 2/W and detects the presence of the second test analyte. The first sensitivity pattern and the second sensitivity pattern and are co-located at the first region, which is the first row along dimension W of the test assay 62 in FIG. 6.

In another implementation of this embodiment, the first sinusoidal sensitivity pattern of the first reagent and the second sinusoidal sensitivity pattern of the second reagent are offset from each other on the substrate 70. In this case, the first reagent in an amount that varies sinusoidally at a first frequency of 3/W as represented by the solid sinusoidal curve A is located at the first row of test assay 62 (FIG. 6) replacing sensitivity pattern 90 and the second reagent in an amount that varies sinusoidally at a second frequency of 2/W as represented by the dashed sinusoidal curve B is located at the second row of the test assay 62 (FIG. 6) replacing sensitivity pattern 91.

In yet another implementation of this embodiment shown in FIG. 8, the second sensitivity pattern has a frequency that is half that of the first sensitivity pattern.

Although specific embodiments have been illustrated and described herein, it will be appreciated by those skilled in the art that any arrangement, which is calculated to achieve the same purpose, may be substituted for the specific embodiment shown. This application is intended to cover any adaptations or variations of the present invention. Therefore, it is manifestly intended that this invention be limited only by the claims and the equivalents thereof.

What is claimed is:

1. A Fourier transform optical detection system for use with a test assay having a sensitivity pattern, the detection system comprising:
    a lens having a Fourier transform plane;
    first and second detectors located in the Fourier transform plane positioned in an arrangement of a Fourier transform pattern of the sensitivity pattern, wherein at least one of the first detectors detect light in at least one peak-intensity region and at least one of the second detectors detect light in at least one low-intensity region; and
    a processor configured to determine an occurrence of a reaction on the test assay when the sensitivity pattern has an intensity variation between the light detected by first detectors in at least one peak intensity region and the light detected by second detectors in at least one low intensity region.

2. The detection system of claim 1, in which the sensitivity pattern forms a spatial filter having a spatial frequency in one dimension, multiples of the spatial frequency in one dimension, submultiples of the spatial frequency in one dimension, the spatial frequency in two dimensions, multiples of the spatial frequency in two dimensions, submultiples of the spatial frequency in two dimensions, and combinations thereof.

3. The detection system of claim 1, wherein the sensitivity pattern comprises a checkerboard pattern.

4. The detection system of claim 1, wherein the sensitivity pattern comprises a sinusoidal pattern in one of one dimension and two dimensions.

5. The detection system of claim 1, in which the sensitivity pattern comprises a uniform array of a pattern.

6. The detection system of claim 1, wherein a first sensitivity pattern located at a first region of the test assay varies sinusoidally at a first frequency and a second sensitivity pattern additionally located at the first region varies sinusoidally at a second frequency, wherein the first region is in one of one dimension and two dimensions.

7. The detection system of claim 1, in which the first and second detectors comprise one of linear arrays of detectors, a two dimensional array of detectors, imaging devices having arrays of pixels, detectors having one size, detectors having various sizes and combinations thereof.

8. The detection system of claim 1, in which the lens comprises one of a cylindrical lens, a spherical lens, an array of cylindrical lenses, an array of spherical lenses, and combinations thereof.

9. A method of increasing a signal to noise ratio during a measurement of a test assay using a Fourier transform detection system, the method comprising:
    receiving light having a sensitivity pattern at a lens having a Fourier transform plane; detecting light in at least one peak-intensity region of a Fourier transform pattern of the sensitivity pattern in the Fourier transform plane;
    detecting light in at least one low-intensity region of the Fourier transform pattern of the sensitivity pattern in the Fourier transform plane; and comparing the light detected by first detectors in at least one peak intensity region with the light detected by second detectors in at least one low intensity region.

10. The method of claim 9, in which the sensitivity pattern is a Fourier transformable pattern, the method further comprising:
forming detection regions on the test assay in the sensitivity pattern, the regions adapted to react to an analyte and to one of emit light, transmit light and reflect light in the sensitivity pattern.

11. The method of claim 10, further comprising:
exposing the test assay to a test material; and
one of emitting light, transmitting light and reflecting light in the sensitivity pattern from an object plane of the lens.

12. The method of claim 9, in which the sensitivity pattern forms a spatial filter having a spatial frequency in one dimension, multiples of the spatial frequency in one dimension, submultiples of the spatial frequency in one dimension, the spatial frequency in two dimensions, multiples of the spatial frequency in two dimensions, submultiples of the spatial frequency in two dimensions, and combinations thereof.

13. The method of claim 9, wherein the sensitivity pattern comprises a uniform array of a pattern.

14. The method of claim 9, wherein the sensitivity pattern comprises a checkerboard pattern.

15. The method of claim 9, wherein the sensitivity pattern comprises a sinusoidal pattern in one of one dimension and two dimensions.

16. The method of claim 9, wherein a first sensitivity pattern to detect the presence of a first test analyte is located at a first region of the test assay and varies sinusoidally at a first frequency and a second sensitivity pattern to detect the presence of a second test analyte is additionally located at the first region and varies sinusoidally at a second frequency.

17. The method of claim 16, wherein the first region is in one of one dimension and two dimensions.

18. A test assay for detecting an analyte, the assay comprising:
a substrate; and
first and second detection regions arranged in a Fourier transformable pattern on the substrate, the first detection regions adapted to react with the analyte and to emit light, transmit light or reflect light in the Fourier transformable pattern, and the second detection regions adapted to not react with the analyte and to emit light, transmit light or reflect light in the Fourier transformable pattern.

* * * * *